(12) United States Patent
Sakamae (10) Patent No.: US 10,410,825 B2
(45) Date of Patent: Sep. 10, 2019

(54) ELECTRON PROBE MICROANALYZER AND STORAGE MEDIUM

(71) Applicant: Shimadzu Corporation, Kyoto (JP)

(72) Inventor: Hiroshi Sakamae, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/991,034

(22) Filed: May 29, 2018

(65) Prior Publication Data

US 2019/0006146 A1 Jan. 3, 2019

(30) Foreign Application Priority Data

Jun. 30, 2017 (JP) ................................ 2017-128850

(51) Int. Cl.
*H01J 37/256* (2006.01)
*G01N 23/2252* (2018.01)

(52) U.S. Cl.
CPC ........ *H01J 37/256* (2013.01); *G01N 23/2252* (2013.01); *G01N 2223/402* (2013.01); *G01N 2223/418* (2013.01); *G01N 2223/605* (2013.01); *H01J 2237/2442* (2013.01); *H01J 2237/2485* (2013.01); *H01J 2237/24425* (2013.01); *H01J 2237/2561* (2013.01)

(58) Field of Classification Search
CPC ............. H01J 37/256; H01J 2237/2442; H01J 2237/2445; H01J 2237/24425; H01J 2237/2584; H01J 2237/2561; G06T 11/005; G06T 11/008; G06T 11/60; G06T 11/206
See application file for complete search history.

(56) References Cited

U.S. PATENT DOCUMENTS

| 2008/0067379 | A1 | 3/2008 | Notoya |
| 2008/0111072 | A1 | 5/2008 | Takakura |
| 2018/0342087 | A1* | 11/2018 | Katoh .................. G06T 11/005 |

FOREIGN PATENT DOCUMENTS

| JP | 2007-285786 A | 11/2007 |
| JP | 2008-122267 A | 5/2008 |
| JP | 2010-107334 A | 5/2010 |
| JP | 2011-227056 A | 11/2011 |

* cited by examiner

*Primary Examiner* — David E Smith
*Assistant Examiner* — Hsien C Tsai
(74) *Attorney, Agent, or Firm* — Maier & Maier, PLLC (57) ABSTRACT

An EDS 5 acquires first spectrum data by detecting an X-ray generated from a sample. A WDS 6 acquires second spectrum data by detecting the X-ray generated from the sample. A phase distribution map generation processing unit 11 generates a phase distribution map of a substance of the sample in a measurement region, on the basis of the first spectrum data acquired with respect to each pixel in the measurement region on a sample surface. A composition information acquisition processing unit 13 acquires element composition information of each phase, on the basis of the second spectrum data acquired with respect to a position on the sample corresponding to a representative pixel in the measurement region corresponding to each of the phases of the phase distribution map.

10 Claims, 6 Drawing Sheets

ELECTRON PROBE MICROANALYZER AND STORAGE MEDIUM

FIELD

The present invention relates to an electron probe microanalyzer detecting an X-ray generated by irradiating a sample with an electron probe with an energy dispersive X-ray spectrometer and a wavelength dispersive X-ray spectrometer, and a storage medium used therein.

BACKGROUND

An energy dispersive X-ray spectrometer (EDS) and a wavelength dispersive X-ray spectrometer (WDS) are known as an X-ray spectrometer used in an electron probe microanalyzer (EPMA).

The EDS is an X-ray spectrometer obtaining an energy spectrum of an X-ray by using a phenomenon that electron-hole pairs of which the number is in proportion to energy are generated according to an internal photoelectric effect when the X-ray is incident on a semiconductor. On the other hand, the WDS utilizes a diffraction phenomenon of an X-ray, and is an X-ray spectrometer detecting only an X-ray of a wavelength satisfying a Bragg's diffraction condition by setting a substance having a multitiered structure with a surface separation, such as a crystal, to a spectroscopic element, and by controlling an incident angle of the X-ray with respect to the spectroscopic element.

In general, the EPMA is provided with a plurality of WDSs, and is configured such that the EDS can be additively provided. In the EPMA provided with both of the WDS and the EDS, features of each of the WDS and the EDS are capable of compensating disadvantages of each other, and thus, it is possible to perform analysis with a higher accuracy (for example, refer to Patent Literatures 1 to 4 described below).

Patent Literature

[Patent Literature 1] JP-A-2007-285786
[Patent Literature 2] JP-A-2008-122267
[Patent Literature 3] JP-A-2010-107334
[Patent Literature 4] JP-A-2011-227056

SUMMARY

The EDS is capable of simultaneously detecting X-rays in all energy ranges. For this reason, the EDS has an advantage that spectrums of all detectable elements can be obtained at significantly small irradiation beam current or for significantly short measurement time compared to the WDS. Recently, a function that spectrums are collected with respect to all measurement points with mapping analysis using the EDS, and a phase distribution map is automatically generated, has appeared according to development in a data processing technology. According to such a function, it is possible to comparatively simply analyze which type of substance exists in a focused region, how the substances are distributed, or which composition generally configures the substance.

On the other hand, the EDS has a disadvantage that an energy resolution is low, and thus, the adjacent peaks easily overlap with each other, or a disadvantage that an S/N ratio is low, and thus, a detection lower limit value is high. For this reason, even in a case where the irradiation beam current increases, or the measurement time increases, it is difficult to detect a trace element or to accurately obtain the composition of the substance.

In the WDS, the peak of the spectrum is sharp, and the S/N ratio is high, and thus, the WDS is applied to detect the trace element or to accurately obtain the composition of the substance. However, only one wavelength can be simultaneously measured by one WDS. For this reason, in a case of analyzing which type of substance exists in the focused region, or how the substances are distributed, for example, follow a procedure in which the existence of the substance of which the composition is different due to a different brightness level of a reflection electron image is confirmed, qualitative analysis is performed with respect to each of the substances by wavelength scanning, and mapping analysis is performed by setting a spectroscopic wavelength with respect to all of the detected elements, and thus, phase analysis is performed by using a result thereof. In such a procedure, there is a case where not only are a large amount of labor and time required, but also the substance having a different composition exists even in a case where the brightness levels of the reflection electron image are the same, and thus, there is a concern that the type of existing substance may be overlooked.

The invention has been made in consideration of such circumstances described above, and an object thereof is to provide an electron probe microanalyzer and a storage medium in which types and a distribution of substances existing in a measurement region, and accurate composition information of each of the substances can be obtained for a comparatively short period of time.

(1) An electron probe microanalyzer according to the invention includes an electron probe irradiation unit, an energy dispersive X-ray spectrometer, a wavelength dispersive X-ray spectrometer, a phase distribution map generation processing unit, and a composition information acquisition processing unit. The electron probe irradiation unit generates an X-ray by irradiating a sample with an electron probe. The energy dispersive X-ray spectrometer acquires first spectrum data by detecting the X-ray generated from the sample. The wavelength dispersive X-ray spectrometer acquires second spectrum data by detecting the X-ray generated from the sample. The phase distribution map generation processing unit generates a phase distribution map of a substance of the sample in a measurement region, on the basis of the first spectrum data acquired with respect to each pixel (each measurement position) on a map in the measurement region on a sample surface. The composition information acquisition processing unit acquires element composition information of each phase, on the basis of the second spectrum data acquired with respect to a position (the measurement position) on the sample corresponding to a representative pixel in the measurement region corresponding to each of the phases of the phase distribution map.

According to such a configuration, it is possible to acquire the first spectrum data with respect to each of the pixels (each of the measurement positions) in the measurement region on the sample surface by the energy dispersive X-ray spectrometer, and to generate the phase distribution map of the substance of the sample in the measurement region for a short period of time, on the basis of the first spectrum data. Then, it is possible to acquire the second spectrum data only with respect to the representative pixel (the measurement position) in the measurement region corresponding to each of the phases of the phase distribution map by the wavelength dispersive X-ray spectrometer, and to acquire accurate element composition information of each of the phases (a high-accuracy element concentration value having a value of a trace element which is difficult to be detected by the energy dispersive X-ray spectrometer), on the basis of the second spectrum data. Therefore, types and a distribution of substances existing in the measurement region, and accurate composition information of each of the substances can be obtained for a comparatively short period of time.

(2) The electron probe microanalyzer may further include a display image generation processing unit. The display image generation processing unit generates a display image by reflecting the element composition information of each of the phases acquired by the composition information acquisition processing unit on each of the phases of the phase distribution map.

According to such a configuration, when the phase distribution map of the substance of the sample in the measurement region is displayed on a display screen, it is possible to display the display image reflecting accurate element composition information of each of the phases on each of the phases of the phase distribution map. Thus, it is possible to display the display image by reflecting accurate element composition information of each of the phases on a phase distribution map of the related art, and thus, it is possible to perform analysis with a higher accuracy.

(3) The electron probe microanalyzer may further include an X-ray intensity map generation processing unit. The X-ray intensity map generation processing unit generates an X-ray intensity map by adjusting a peak wavelength condition of the wavelength dispersive X-ray spectrometer with respect to each of the detected elements, on the basis of the element composition information of each of the phases acquired by the composition information acquisition processing unit, and by measuring an X-ray intensity of each of the pixels in the measurement region.

According to such a configuration, it is possible to select only the element which contains the trace element difficult to be detected by the energy dispersive spectrometer and is actually detected in the measurement region, on the basis of accurate element composition information of each of the phases, and to generate the X-ray intensity map in the measurement region with respect to the element.

(4) The electron probe microanalyzer may further include an average value calculation processing unit and an average element concentration calculation processing unit. The average value calculation processing unit calculates an average value of X-ray intensities of a peak wavelength with respect to a pixel in a range of each of the phases, on the basis of the X-ray intensity map. The average element concentration calculation processing unit calculates an average element concentration of each of the phases by comparing the average value of the X-ray intensities of the peak wavelength calculated by the average value calculation processing unit with an X-ray intensity of a peak wavelength in a case where a concentration is known.

According to such a configuration, it is possible to calculate the average value of the X-ray intensities of the peak wavelength based on the X-ray intensity map, with respect to the pixel in the range of each of the phases of the phase distribution map, and to calculate the average element concentration of each of the phases on the basis of the average value. It is possible to reduce an influence of a fluctuation in a measurement value of each of the pixels due to a statistical fluctuation by averaging the X-ray intensities with respect to the pixel in the range of each of the phases, and thus, it is possible to obtain the element concentration value with a higher accuracy.

(5) The X-ray intensity map generation processing unit may generate an X-ray intensity map of a peak wavelength and an X-ray intensity map of an background wavelength by adjusting a peak wavelength condition and a background wavelength condition of the wavelength dispersive X-ray spectrometer with respect to each of the detected elements, on the basis of the element composition information of each of the phases acquired by the composition information acquisition processing unit, and by measuring an X-ray intensity of each of the peak wavelength and the background wavelength of each of the pixels in the measurement region. In this case, the average value calculation processing unit may calculate the average value of the X-ray intensities of each of the peak wavelength and the background wavelength with respect to pixel in the range of each of the phases, on the basis of the X-ray intensity map of the peak wavelength and the X-ray intensity map of the background wavelength. In addition, the average element concentration calculation processing unit may calculate the average element concentration of each of the phases by comparing a result obtained by subtracting the average value of the X-ray intensities of the background wavelength from the average value of the X-ray intensities of the peak wavelength calculated by the average value calculation processing unit with a height of a peak in a case where a concentration is known (a value obtained by subtracting the X-ray intensity of the background wavelength from the X-ray intensity of the peak wavelength).

According to such a configuration, it is possible to calculate not only the average value of the X-ray intensities of the peak wavelength but also the average value of the X-ray intensities of the background wavelength with respect to the pixel in the range of each of the phases of the phase distribution map, and to calculate the average element concentration of each of the phases by using a difference between the average value of the X-ray intensities of the peak wavelength and the average value of the X-ray intensities of the background wavelength. It is possible to obtain a value having a high accuracy in which the influence of the fluctuation in the measurement value of each of the pixels due to the statistical fluctuation is reduced, with respect to not only the X-ray intensity of the peak wavelength but also a background intensity, and to obtain the element concentration value having a high accuracy in which an influence of a background is also suitably excluded.

(6) A storage medium according to the invention, storing a data processing program used for an electron probe microanalyzer, which includes an electron probe irradiation unit generating an X-ray by irradiating a sample with an electron probe, an energy dispersive X-ray spectrometer acquiring first spectrum data by detecting the X-ray generated from the sample, and a wavelength dispersive X-ray spectrometer acquiring second spectrum data by detecting the X-ray generated from the sample, allows a computer to function as a phase distribution map generation processing unit and a composition information acquisition processing unit. The phase distribution map generation processing unit generates a phase distribution map of a substance of the sample in a measurement region, on the basis of the first spectrum data acquired with respect to each pixel (each measurement position) on a map in the measurement region on a sample surface. The composition information acquisition processing unit acquires element composition information of each phase, on the basis of the second spectrum data acquired with respect to a position (the measurement position) on the sample corresponding to a representative pixel in the measurement region corresponding to each of the phases of the phase distribution map.

(7) The storage medium may further allow the computer to function as a display image generation processing unit. The display image generation processing unit generates a display image by reflecting the element composition information of each of the phases acquired by the composition information acquisition processing unit on each of the phases of the phase distribution map.

(8) The storage medium may further allow the computer to function as an X-ray intensity map generation processing unit. The X-ray intensity map generation processing unit generates an X-ray intensity map by adjusting a peak wavelength condition of the wavelength dispersive X-ray spectrometer with respect to each of the detected elements, on the basis of the element composition information of each of the phases acquired by the composition information acquisition processing unit, and by measuring an X-ray intensity of each of the pixels in the measurement region.

(9) The storage medium may further allow the computer to function as an average value calculation processing unit and an average element concentration calculation processing unit. The average value calculation processing unit calculates an average value of X-ray intensities of a peak wavelength with respect to a pixel in a range of each of the phases, on the basis of the X-ray intensity map. The average element concentration calculation processing unit calculates an average element concentration of each of the phases by comparing the average value of the X-ray intensities of the peak wavelength calculated by the average value calculation processing unit with an X-ray intensity of a peak wavelength in a case where a concentration is known.

(10) The X-ray intensity map generation processing unit may generate an X-ray intensity map of a peak wavelength and an X-ray intensity map of an background wavelength by adjusting a peak wavelength condition and a background wavelength condition of the wavelength dispersive X-ray spectrometer with respect to each of the detected elements, on the basis of the element composition information of each of the phases acquired by the composition information acquisition processing unit, and by measuring an X-ray intensity of each of the peak wavelength and the background wavelength of each of the pixels in the measurement region. In this case, the average value calculation processing unit may calculate the average value of the X-ray intensities of each of the peak wavelength and the background wavelength with respect to pixel in the range of each of the phases, on the basis of the X-ray intensity map of the peak wavelength and the X-ray intensity map of the background wavelength. In addition, the average element concentration calculation processing unit may calculate the average element concentration of each of the phases by comparing a result obtained by subtracting the average value of the X-ray intensities of the background wavelength from the average value of the X-ray intensities of the peak wavelength calculated by the average value calculation processing unit with a height of a peak in a case where a concentration is known (a value obtained by subtracting the X-ray intensity of the background wavelength from the X-ray intensity of the peak wavelength).

According to the invention, it is possible to obtain the phase distribution map for a comparatively short period of time, on the basis of the first spectrum data acquired by the energy dispersive X-ray spectrometer with respect to each of the pixels (each of the measurement positions) in the measurement region on the sample surface, to acquire the second spectrum data in the representative position of each of the phases of the phase distribution map by using the wavelength dispersive spectrometer, and thus, to acquire accurate element composition information of each of the phases (a high-accuracy element concentration value having a value of a trace element which is difficult to be detected by the energy dispersive X-ray spectrometer).

In addition, the X-ray intensity map is acquired with respect to each of the detected elements by the wavelength dispersive X-ray spectrometer, on the basis of the accurate element composition information of each of the phases, obtained as described above, and thus, it is possible to acquire the X-ray intensity map of the element also containing the trace element difficult to be detected by the energy dispersive X-ray spectrometer.

Further, the average value of the X-ray intensity maps is calculated with respect to the pixel in the range of each of the phases of the phase distribution map, and the average element concentration of each of the phases is calculated on the basis of the average value, and thus, it is possible to obtain the element concentration value having a high accuracy in which the fluctuation in the measurement value of each of the pixels due to the statistical fluctuation is reduced.

Further, the X-ray intensity map is acquired at not only the peak wavelength of each of the detected elements but also the background wavelength, and the average value is calculated with respect to the pixel in the range of each of the phases of the phase distribution map, and similarly, the average element concentration is calculated from the value obtained by being subtracted from the average value obtained with respect to the peak wavelength, and thus, it is possible to obtain the element concentration value having a high accuracy with respect to the background intensity, in which the influence of the fluctuation in the measurement value of each of the elements due to the statistical fluctuation is reduced, and the influence of the background is suitably excluded.

DETAILED DESCRIPTION OF THE DRAWINGS

1. Entire Configuration of Electron Probe Microanalyzer

Figure 1:
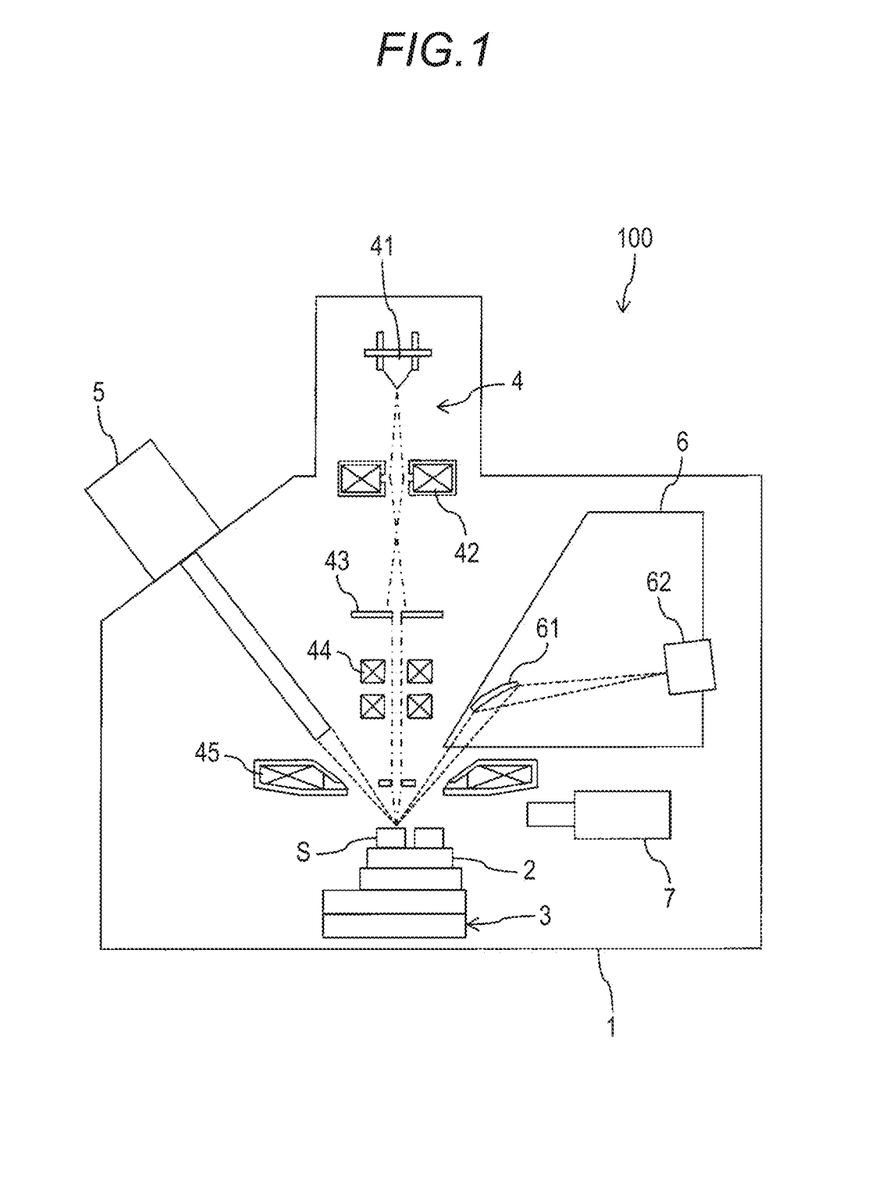
FIG. 1 is a schematic view illustrating a configuration example of an EPMA according to one embodiment of the invention.

FIG. 1 is a schematic view illustrating a configuration example of an EPMA 100 according to one embodiment of the invention. The electron probe microanalyzer (EPMA) 100 is a device for performing analysis by disposing a sample S in a housing 1, by irradiating the sample S with an electron probe, and by detecting an X-ray generated from the sample S. The EPMA 100 includes a sample holder 2, a sample stage 3, an electron probe irradiation unit 4, an EDS 5, a WDS 6, a secondary electron detector 7, and the like.

The sample holder 2 is a member for retaining the sample, and is detachable with respect to the sample stage 3. The sample stage 3 can be displaced along two axes (an X axis and a Y axis) orthogonal to each other in a horizontal surface, and a Z axis in a vertical direction. By controlling the displacement of the sample stage 3, it is possible to adjust a measurement region (a region irradiated with the electron probe) on the surface of the sample S.

The electron probe irradiation unit 4 includes an electron source 41, a capacitor lens 42, a diaphragm 43, a scanning coil 44, an object lens 45, and the like. The electron probe ejected from the electron source 41 is condensed by the capacitor lens 42, a light flux is diaphragmed by the diaphragm 43, and then, the electron probe is formed into the shape of a small spot by the object lens 45, and thus, is applied onto the surface of the sample S. The electron probe applied onto the surface of the sample S is scanned in a horizontal direction (an X direction and a Y direction) in the measurement region by the scanning coil 44. The X-ray is generated from the surface of the sample S irradiated with the electron probe, and the X-ray is incident on the EDS 5 and the WDS 6.

The EDS 5 is a spectrometer (an energy dispersive X-ray spectrometer) obtaining an energy spectrum of the X-ray, and includes a semiconductor detector and a multichannel analyzer (not illustrated). The X-ray from the sample S is incident on the semiconductor detector, and is converted into an electric signal, and a pulse of a height in proportion to the energy of the incident X-ray is led to the multichannel analyzer. Accordingly, it is possible to acquire data of an X-ray spectrum (first spectrum data) by integrating the number of pulses into each channel corresponding to X-ray energy. The EDS 5 is detachable from the outside of the housing 1, and can be additively provided in the EPMA 100.

The WDS 6 is a spectrometer (a wavelength dispersive X-ray spectrometer) using a diffraction phenomenon of the X-ray, and includes a spectroscopic crystal 61 and an X-ray detector 62. The X-ray from the sample S is dispersed by the spectroscopic crystal 61 as a spectroscopic element, and is incident on the X-ray detector 62. At this time, an incident angle of the X-ray with respect to the spectroscopic crystal 61 is controlled, and thus, it is possible to detect only an X-ray of a wavelength satisfying a Bragg's diffraction condition by the X-ray detector 62, and to acquire the data of the X-ray spectrum (second spectrum data). A plurality of WDSs 6 are provided in the housing 1. Accordingly, elements of which the number is identical to the number of WDSs 6 can be simultaneously analyzed.

The secondary electron detector 7 detects a secondary electron which is generated from the surface of the sample S. A secondary electron image can be obtained on the basis of a detection signal from the secondary electron detector 7. Here, the secondary electron detector 7 may not be provided.

2. Electric Configuration of Electron Probe Microanalyzer

Figure 2:
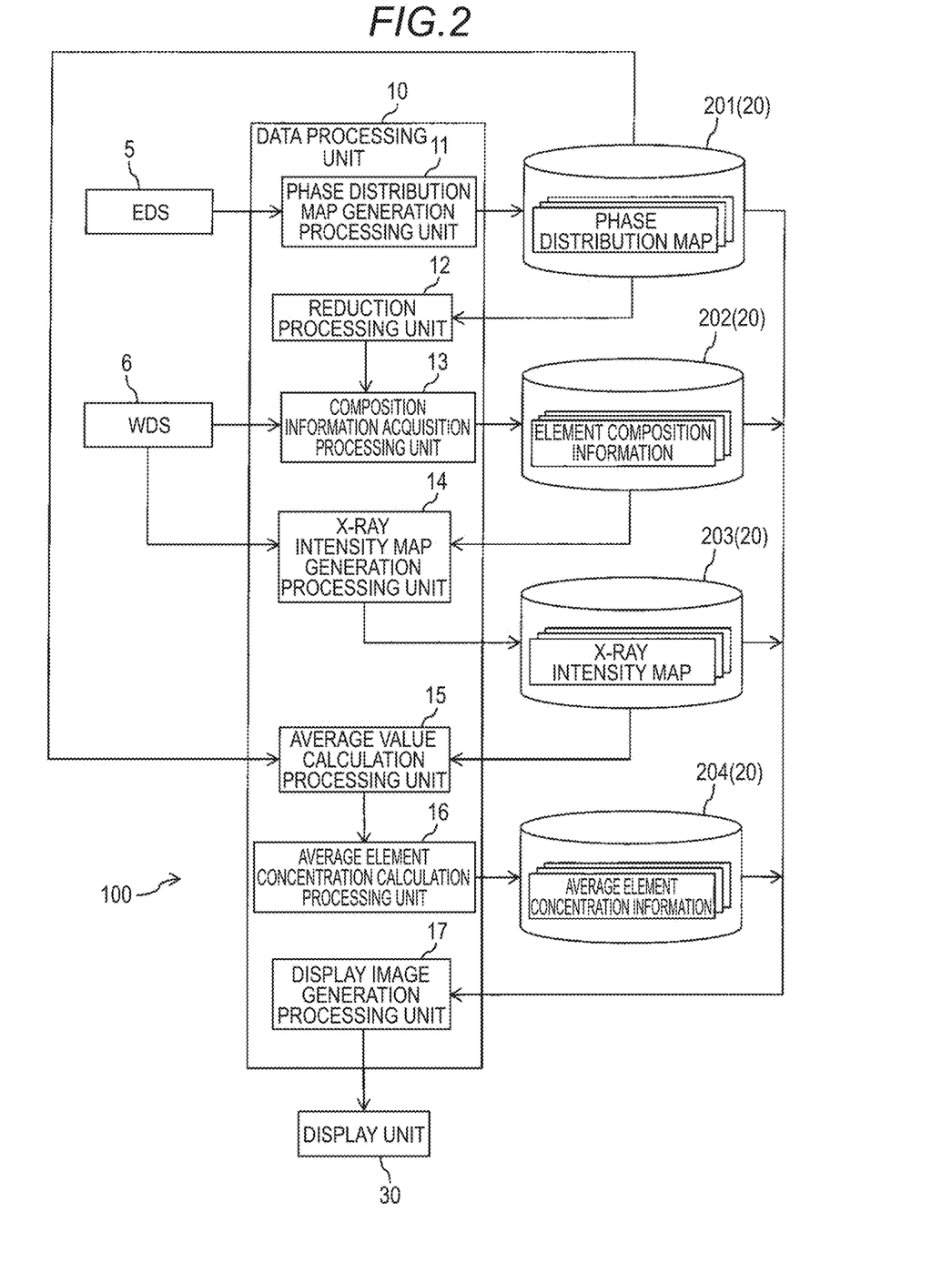
FIG. 2 is a block diagram illustrating an example of an electric configuration of the EPMA of FIG. 1.

FIG. 2 is a block diagram illustrating an example of an electric configuration of the EPMA 100 of FIG. 1. The EPMA includes a data processing unit 10, a storage unit 20, a display unit 30, and the like, in addition to the EDS 5 and the WDS 6 described above.

The data processing unit 10, for example, includes a central processing unit (CPU), and performs processing with respect to data input from the EDS 5 and the WDS 6. The CPU executes a program, and thus, the data processing unit 10 functions as a phase distribution map generation processing unit 11, a reduction processing unit 12, a composition information acquisition processing unit 13, an X-ray intensity map generation processing unit 14, an average value calculation processing unit 15, an average element concentration calculation processing unit 16, a display image generation processing unit 17, and the like.

In this embodiment, a case is described in which the number of data processing units 10 is 1, but for example, an EPMA control device controlling the entire operation of the EPMA 100 including the WDS 6, and an EDS control device controlling the operation of the additively provided EDS 5 may be provided, and the data processing unit 10 may be configured of an EPMA data processing device performing input and output of data with respect to the EPMA control device, and an EDS data processing device performing input and output of data with respect to the EDS control device.

The storage unit 20, for example, is configured of a random access memory (RAM) or a hard disk. A phase distribution map storage unit 201, an element composition information storage unit 202, an X-ray intensity map storage unit 203, an average element concentration information storage unit 204, and the like are assigned to a storage region of the storage unit 20. The display unit 30, for example, is configured of a liquid crystal display device.

3. Specific Example of Phase Distribution Map

The phase distribution map generation processing unit 11 generates a phase distribution map of a substance of the sample S in the measurement region, on the basis of spectrum data acquired by the EDS 5. Data of the generated phase distribution map is stored in the phase distribution map storage unit 201.

Figure 3:
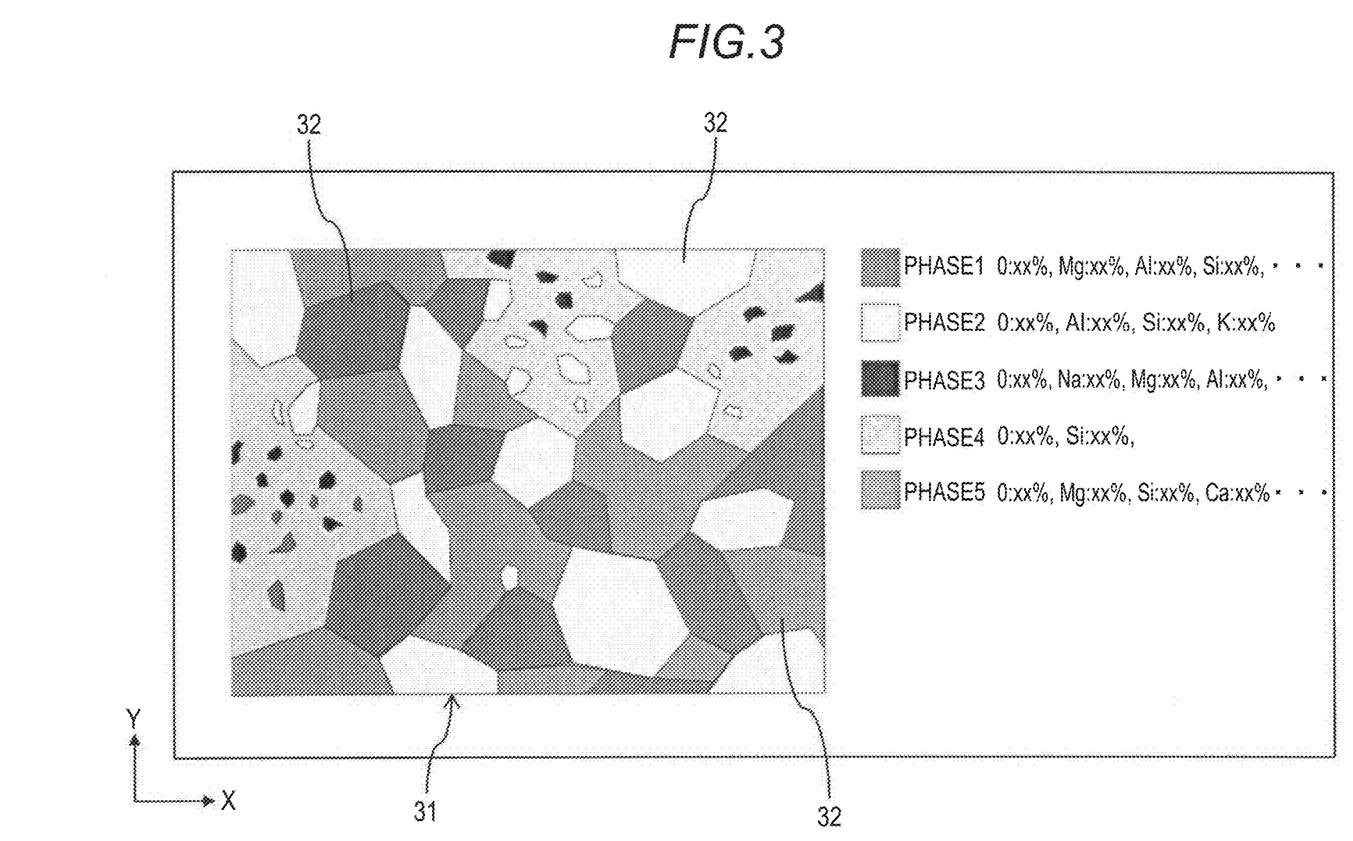
FIG. 3 is a schematic view illustrating a specific example of a phase distribution map.

FIG. 3 is a schematic view illustrating a specific example of the phase distribution map. A measurement region 31 is a rectangular region set on the surface of the sample S, and is formed of a plurality of pixels (measurement positions) arranged into the shape of a matrix in the X direction and the Y direction. The electron probe is scanned in the measurement region 31, and thus, the first spectrum data of each of the pixels is obtained. The phase distribution map generation processing unit 11 generates the phase distribution map of the substance of the sample in the measurement region 31 as exemplified in FIG. 3, on the basis of the first spectrum data acquired with respect to each of the pixels.

In the phase distribution map, the measurement region 31 is divided into a plurality of types of phases 32. That is, the measurement region 31 is divided such that pixels having the same composition have the same phase, on the basis of the first spectrum data acquired with respect to each of the pixels in the measurement region 31. Thus, it is possible to obtain the phase distribution map indicating which type of substance exists in the measurement region 31, how the substances are distributed, or which composition generally configures the substance, on the basis of the first spectrum data obtained from the EDS 5.

The display image generation processing unit 17 reads out the data of the phase distribution map stored in the phase distribution map storage unit 201, and generates a display image of the phase distribution map, and thus, it is possible to display the display image on the display unit 30. Each of the phases 32 divided into the measurement region 31, for example, is displayed on the display unit 30 by being distinguished in different aspects such as different color or different concentrations.

4. Reduction Processing

The reduction processing unit 12 performs processing of selecting a representative pixel of each of the phases 32 in the measurement region 31, on the basis of the data of the phase distribution map stored in the phase distribution map storage unit 201. The reduction processing unit 12, first, performs processing of binarizing the data of each of the phases 32 of the phase distribution map, in order to select the representative pixel of each of the phases 32.

Figure 4:
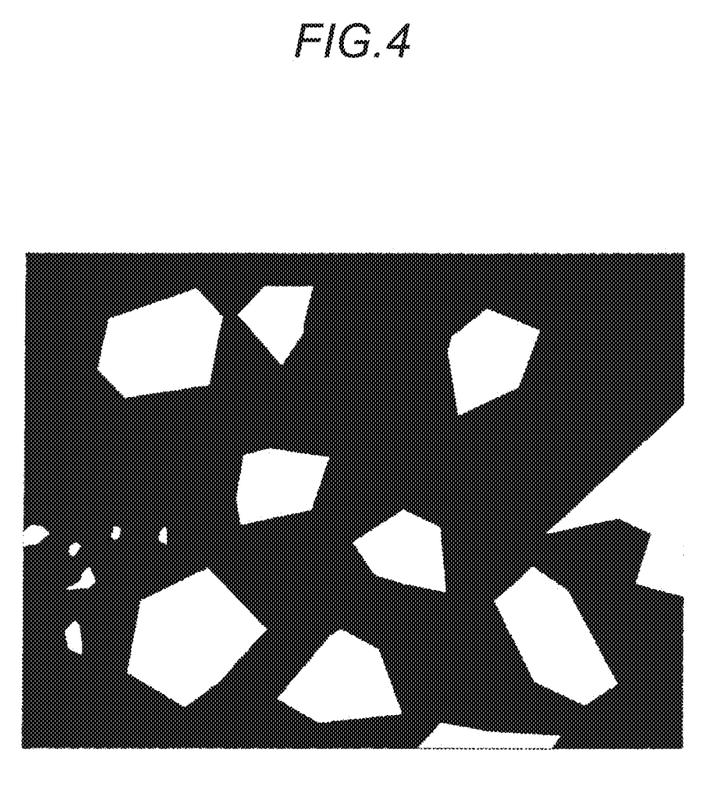
FIG. 4 is a schematic view illustrating an example of the phase distribution map in a state where one phase in a measurement region is binarized.

FIG. 4 is a schematic view illustrating an example of the phase distribution map in a state where one phase 32 in the measurement region 31 is binarized. Thus, a region corresponding to one phase 32 in the measurement region 31 is set to be white, and the other region in the measurement region 31 is set to be black, and thus, the entire measurement region 31 is binarized.

After that, reduction processing of converting a white pixel, which is a boundary with a black pixel, into the black pixel one by one, for each of the divided regions, and thus, the finally remaining black pixel is selected as the representative pixel. Such processing is sequentially performed with respect to each of the phases 32 in the measurement region 31, and the representative pixel of each of the phases 32 is selected.

The composition information acquisition processing unit 13 acquires the second spectrum data by the WDS 6 with respect to each of the positions (the measurement positions) on the sample S corresponding to the representative pixel selected by the reduction processing, and acquires element composition information of each of the phases 32, on the basis of the second spectrum data. At this time, in a case of increasing a spot diameter of the electron probe applied onto the surface of the sample S from the electron probe irradiation unit 4 within a range where the phase does not protrude around the representative pixel (the position) of each of the phases 32, and thus, it is possible to obtain an average composition result.

In this embodiment, it is possible to acquire the first spectrum data with respect to each of the pixels (each of the measurement positions) in the measurement region 31 on the surface of the sample S by the EDS 5, and it is possible to generate the phase distribution map of the substance of the sample S in the measurement region 31 for a short period of time, on the basis of the first spectrum data. Then, it is possible to acquire the second spectrum data only with respect to the representative pixel (the measurement position) in the measurement region 31 corresponding to each of the phases 32 of the phase distribution map by the WDS 6, and it is possible to acquire accurate element composition information of each of the phases 32 (a high-accuracy element concentration value including a value of a trace element which is difficult to be detected by the energy dispersive X-ray spectrometer), on the basis of the second spectrum data. Therefore, it is possible to obtain types and a distribution of substances existing in the measurement region 31, and accurate composition information of each of the substances for a comparatively short period of time.

The data of the element composition information acquired by the composition information acquisition processing unit 13 is stored in the element composition information storage unit 202. The display image generation processing unit 17 reads out the data of the element composition information stored in the element composition information storage unit 202, and generates the display image, and thus, is capable of displaying the display image on the display unit 30.

The display image generation processing unit 17 may generate the display image by reflecting the element composition information of each of the phases 32 acquired by the composition information acquisition processing unit 13 on each of the phases 32 of the phase distribution map. That is, composition information of each of the phases 32 in the phase distribution map may be the element composition information of each of the phases 32 acquired by the composition information acquisition processing unit 13. In this case, when the phase distribution map of the substance of the sample S in the measurement region 31 is displayed on the display screen, it is possible to display the display image reflecting accurate element composition information of each of the phases 32 on each of the phases 32 of the phase distribution map. Thus, it is possible to display the display image by reflecting accurate element composition information on each of the phases of the phase distribution map of the related art, and thus, it is possible to perform analysis with a higher accuracy.

5. Specific Example of X-Ray Intensity Map

The X-ray intensity map generation processing unit 14 generates an X-ray intensity map by measuring the intensity of the X-ray to be detected by the X-ray detector 62 of the WDS 6, with respect to each of the detected elements, on the basis of element composition information of the each of the phases 32 acquired by the composition information acquisition processing unit 13. The generated X-ray intensity map is stored in the X-ray intensity map storage unit 203.

Specifically, a spectroscopic wavelength condition of the WDS 6 is set to a peak wavelength corresponding to the selected element, and the intensity of the X-ray to be detected by the X-ray detector 62 is measured with respect to each of the pixels in the measurement region 31, and thus, the X-ray intensity map is generated. Accordingly, it is possible to select only an element which contains the trace element difficult to be detected by the energy dispersive spectrometer and is actually detected in measurement region, on the basis of accurate element composition information of each of the phases 32, and to generate the X-ray intensity map in the measurement region 31 with respect to the element. Furthermore, the X-ray intensity is a value in proportion to the intensity of the X-ray to be detected by the X-ray detector 62, and for example, is a count value of the X-ray per constant time in the X-ray detector 62.

Figure 5:
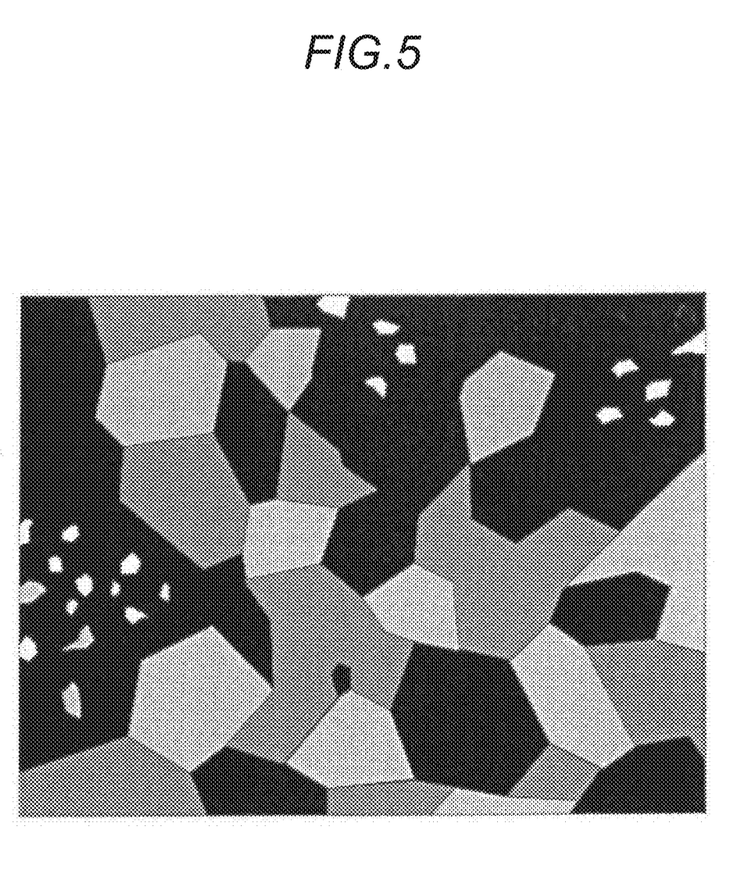
FIG. 5 is a schematic view illustrating a specific example of an X-ray intensity map.

FIG. 5 is a schematic view illustrating a specific example of the X-ray intensity map. The display image generation processing unit 17 reads out the data of the X-ray intensity map stored in the X-ray intensity map storage unit 203, and generates the display image of the X-ray intensity map, and thus, is capable of displaying the display image on the display unit 30. Each of the pixels in the measurement region 31 is displayed on the display unit 30 in an aspect different according to the X-ray intensity, such as a color or a concentration corresponding to the X-ray intensity in the pixel.

6. Average Value Calculation Processing

The average value calculation processing unit 15 calculates an average value of the X-ray intensities of the peak wavelength with respect to the pixel in the range of each of the phases 32, on the basis of the X-ray intensity map stored in the X-ray intensity map storage unit 203.

Figure 6:
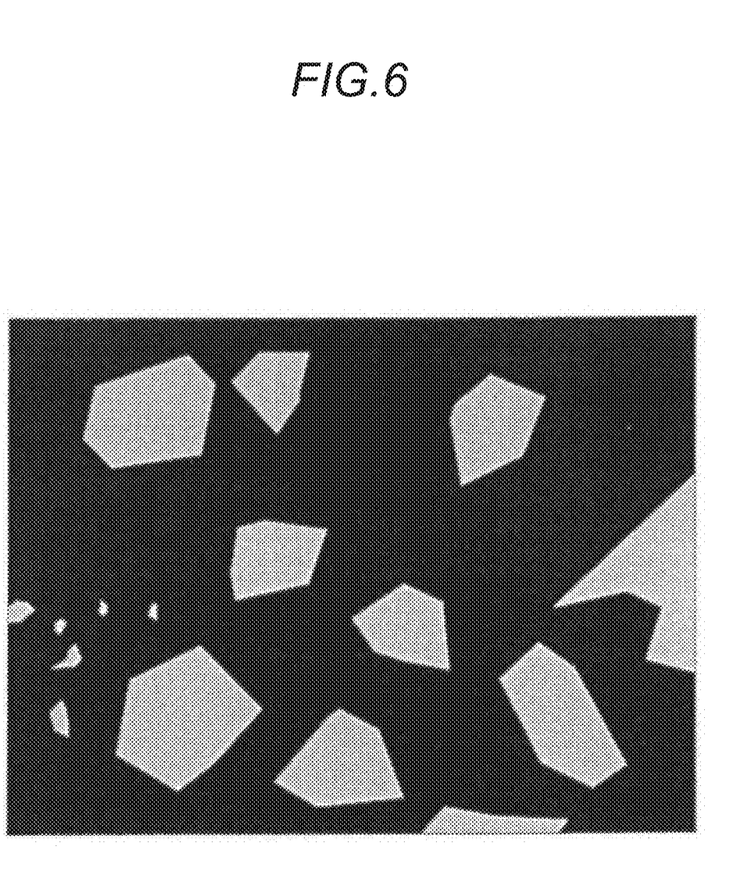
FIG. 6 is a diagram in which only a pixel in a region corresponding to one phase in the measurement region is extracted from the X-ray intensity map of FIG. 5.

FIG. 6 is a diagram in which only the pixel of the region corresponding to one phase 32 in the measurement region 31 is extracted from the X-ray intensity map of FIG. 5. Thus, the X-ray intensity of the peak wavelength is integrated with respect to only the pixel of the region corresponding to each of the phases 32 obtained from the phase distribution map (in this example, the region corresponding to FIG. 4), in each of the pixels in the measurement region 31, and the integrated value is divided for the total measurement time of the phase 32, and thus, the average value is calculated.

7. Average Element Concentration Calculation Processing

The average element concentration calculation processing unit 16 calculates an average element concentration (an element content) of each of the phases 32, on the basis of the average value of the X-ray intensities of the peak wavelength calculated by the average value calculation processing unit 15. Specifically, the average value of the X-ray intensities of the peak wavelength calculated by the average value calculation processing unit 15 is compared with an X-ray intensity of a peak wavelength in a case where a concentration is known, and thus, the concentration of the element is calculated.

Thus, in this embodiment, it is possible to calculate the average value of the X-ray intensities of the peak wavelength based on the X-ray intensity map with respect to the pixel in the range of the each of the phases 32 of the phase distribution map, and to calculate the average element concentration of each of the phases 32 on the basis of the average value. By averaging the X-ray intensities with respect to the pixel in the range of each of the phases 32, it is possible to reduce an influence of a fluctuation in a measurement value of each of the pixels due to a statistical fluctuation, and thus, it is possible to obtain an element concentration value with a higher accuracy.

The concentration of the element of each of the phases 32 calculated by the average element concentration calculation processing unit 16 is stored in the average element concentration information storage unit 204, as average element concentration information. The display image generation processing unit 17 is capable of reading out the average element concentration information stored in the average element concentration information storage unit 204, and is capable of generating the display image by reflecting the average element concentration information on the phase distribution map. In this case, the average element concentration of each of the phases 32 calculated by the average element concentration calculation processing unit 16 may be displayed on the display unit 30, as the composition information of each of the phases 32 of the phase distribution map.

8. Modification Example

In the embodiment described above, a case has been described in which the spectroscopic wavelength condition of the WDS 6 is set to the peak wavelength corresponding to the selected element, and the intensity of the X-ray to be detected by the X-ray detector 62 of the WDS 6 is measured, and thus, only the X-ray intensity map of the peak wavelength is generated. However, an X-ray intensity map with respect to not only the X-ray intensity on the apex of the peak (the X-ray intensity of the peak wavelength), but also an X-ray intensity on the skirt of the peak (an X-ray intensity of a background wavelength) may be generated.

In this case, the X-ray intensity map generation processing unit 14 generates the X-ray intensity map of the peak wavelength and the X-ray intensity map of the background wavelength by adjusting a peak wavelength condition and a background wavelength condition of the WDS 6 with respect to each of the detected elements, on the basis of the element composition information of each of the phases 32 acquired by the composition information acquisition processing unit 13, and by measuring the X-ray intensity of each of the peak wavelength and the background wavelength of each of the pixels in the measurement region 31. Each of the generated X-ray intensity distributions is stored in the X-ray intensity map storage unit 203.

The average value calculation processing unit 15 calculates each of the average value of the X-ray intensities of the peak wavelength with respect to the pixel in the range of each of each of the phases 32, and the average value of the X-ray intensities of the background wavelength, on the basis of the X-ray intensity map stored in the X-ray intensity map storage unit 203. Then, the average element concentration of each of the phases 32 is calculated by the average element concentration calculation processing unit 16, on the basis of the calculated average value of the X-ray intensities of the peak wavelength and the background wavelength.

Specifically, a result obtained by subtracting the average value of the X-ray intensities of the background wavelength from the average value of the X-ray intensities of the peak wavelength is compared to the height of the peak in a case where the concentration is known (a value obtained by subtracting the X-ray intensity of the background wavelength from the X-ray intensity of the peak wavelength), and thus, the average element concentration of each of the phases 32 is calculated. In this case, the influence of the fluctuation in the measurement value of each of the elements due to the statistical fluctuation is also reduced with respect to a background intensity, and is subtracted from the average value of the X-ray intensities of the peak wavelength, and thus, it is possible to obtain a high-accuracy element concentration value in which the influence of the background is suitably excluded. Here, the average element concentration of each of the phases 32 may be calculated on the basis of the average value of the X-ray intensities of the peak wavelength, and only in a case where the average element concentration is less than or equal to a constant value, the X-ray intensity map of the background wavelength may be acquired, and the average value of the X-ray intensities may be used as the background intensity.

In the embodiment described above, the EPMA 100 including the data processing unit 10 has been described, but a program for allowing a computer to function as the data processing unit 10 (a data processing program) can also be provided. In this case, the program may be provided in a state or being stored in a storage medium, or the program itself may be provided through wired communication or wireless communication.

The invention claimed is:

1. An electron probe microanalyzer, comprising:
an electron probe irradiation unit generating an X-ray by irradiating a sample with an electron probe;
an energy dispersive X-ray spectrometer acquiring first spectrum data by detecting the X-ray generated from the sample;
a wavelength dispersive X-ray spectrometer acquiring second spectrum data by detecting the X-ray generated from the sample;
a phase distribution map generation processing unit generating a phase distribution map of a substance of the sample in a measurement region, on the basis of the first spectrum data acquired with respect to each pixel in the measurement region on a sample surface; and
a composition information acquisition processing unit acquiring element composition information of each phase, on the basis of the second spectrum data acquired with respect to a position on the sample corresponding to a representative pixel in the measurement region corresponding to each of the phases of the phase distribution map.

2. The electron probe microanalyzer according to claim 1, further comprising:
a display image generation processing unit generating a display image by reflecting the element composition information of each of the phases acquired by the composition information acquisition processing unit on each of the phases of the phase distribution map.

3. The electron probe microanalyzer according to claim 1, further comprising:

an X-ray intensity map generation processing unit generating an X-ray intensity map by adjusting a peak wavelength condition of the wavelength dispersive X-ray spectrometer with respect to each of the detected elements, on the basis of the element composition information of each of the phases acquired by the composition information acquisition processing unit, and by measuring an X-ray intensity of each of the pixels in the measurement region.

4. The electron probe microanalyzer according to claim 3, further comprising:
an average value calculation processing unit calculating an average value of X-ray intensities of a peak wavelength with respect to a pixel in a range of each of the phases, on the basis of the X-ray intensity map; and
an average element concentration calculation processing unit calculating an average element concentration of each of the phases by comparing the average value of the X-ray intensities of the peak wavelength calculated by the average value calculation processing unit with an X-ray intensity of a peak wavelength in a case where a concentration is known.

5. The electron probe microanalyzer according to claim 4, wherein the X-ray intensity map generation processing unit generates an X-ray intensity map of a peak wavelength and an X-ray intensity map of a background wavelength by adjusting a peak wavelength condition and a background wavelength condition of the wavelength dispersive X-ray spectrometer with respect to each of the detected elements, on the basis of the element composition information of each of the phases acquired by the composition information acquisition processing unit, and by measuring an X-ray intensity of each of the peak wavelength and the background wavelength of each of the pixels in the measurement region,
the average value calculation processing unit calculates an average value of the X-ray intensities of each of the peak wavelength and the background wavelength with respect to the pixel in the range of each of the phases, on the basis of the X-ray intensity map of the peak wavelength and the X-ray intensity map of the background wavelength, and
the average element concentration calculation processing unit calculates the average element concentration of each of the phases by comparing a result obtained by subtracting the average value of the X-ray intensities of the background wavelength from the average value of the X-ray intensities of the peak wavelength calculated by the average value calculation processing unit with a height of a peak in a case where a concentration is known.

6. A storage medium storing a data processing program used for an electron probe microanalyzer, which includes an electron probe irradiation unit generating an X-ray by irradiating a sample with an electron probe, an energy dispersive X-ray spectrometer acquiring first spectrum data by detecting the X-ray generated from the sample, and a wavelength dispersive X-ray spectrometer acquiring second spectrum data by detecting the X-ray generated from the sample, the medium allowing a computer to function as:
a phase distribution map generation processing unit generating a phase distribution map of a substance of the sample in a measurement region, on the basis of the first spectrum data acquired with respect to each pixel in the measurement region on a sample surface; and
a composition information acquisition processing unit acquiring element composition information of each phase, on the basis of the second spectrum data acquired with respect to a position on the sample corresponding to a representative pixel in the measurement region corresponding to each of the phases of the phase distribution map.

7. The storage medium according to claim 6, further allowing the computer to function as:
a display image generation processing unit generating a display image by reflecting the element composition information of each of the phases acquired by the composition information acquisition processing unit on each of the phases of the phase distribution map.

8. The storage medium according to claim 6, further allowing the computer to function as:
an X-ray intensity map generation processing unit generating an X-ray intensity map by adjusting a peak wavelength condition of the wavelength dispersive X-ray spectrometer with respect to each of the detected elements, on the basis of the element composition information of each of the phases acquired by the composition information acquisition processing unit, and by measuring an X-ray intensity of each of the pixels in the measurement region.

9. The storage medium according to claim 8, further allowing the computer to function as:
an average value calculation processing unit calculating an average value of X-ray intensities of a peak wavelength with respect to a pixel in a range of each of the phases, on the basis of the X-ray intensity map; and
an average element concentration calculation processing unit calculating an average element concentration of each of the phases by comparing the average value of the X-ray intensities of the peak wavelength calculated by the average value calculation processing unit with an X-ray intensity of a peak wavelength in a case where a concentration is known.

10. The storage medium according to claim 9, wherein the X-ray intensity map generation processing unit generates an X-ray intensity map of a peak wavelength and an X-ray intensity map of a background wavelength by adjusting a peak wavelength condition and a background wavelength condition of the wavelength dispersive X-ray spectrometer with respect to each of the detected elements, on the basis of the element composition information of each of the phases acquired by the composition information acquisition processing unit, and by measuring an X-ray intensity of each of the peak wavelength and the background wavelength of each of the pixels in the measurement region,
the average value calculation processing unit calculates an average value of the X-ray intensities of each of the peak wavelength and the background wavelength with respect to the pixel in the range of each of the phases, on the basis of the X-ray intensity map of the peak wavelength and the X-ray intensity map of the background wavelength, and
the average element concentration calculation processing unit calculates the average element concentration of each of the phases by comparing a result obtained by subtracting the average value of the X-ray intensities of the background wavelength from the average value of the X-ray intensities of the peak wavelength calculated by the average value calculation processing unit with a height of a peak in a case where a concentration is known.

* * * * *